(12) United States Patent
Szymczak

(10) Patent No.: US 8,309,118 B2
(45) Date of Patent: Nov. 13, 2012

(54) FILM FORMING COMPOSITIONS CONTAINING SUCRALOSE

(75) Inventor: Christopher E. Szymczak, Marlton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 748 days.

(21) Appl. No.: 10/176,832

(22) Filed: Jun. 21, 2002

(65) Prior Publication Data

US 2003/0108607 A1    Jun. 12, 2003

Related U.S. Application Data

(60) Provisional application No. 60/325,727, filed on Sep. 28, 2001.

(51) Int. Cl.
*A61K 35/68* (2006.01)
*A61K 31/715* (2006.01)
*A61K 31/35* (2006.01)

(52) U.S. Cl. .......................... 424/441; 514/54; 514/451

(58) Field of Classification Search .................. 424/474, 424/441; 514/54, 451
See application file for complete search history.

(56) References Cited

U.S. PATENT DOCUMENTS

| | | | |
|---|---|---|---|
| 1,787,777 A | 12/1926 | Colton | |
| 3,185,626 A | 5/1965 | Baker | |
| 3,652,294 A | 3/1972 | Marotta et al. | |
| 3,751,277 A | 8/1973 | Small et al. | |
| 3,802,896 A | 4/1974 | Westall et al. | |
| 4,001,211 A | 1/1977 | Sarkar | |
| 4,267,164 A | 5/1981 | Yeh et al. | |
| 4,313,765 A | 2/1982 | Baird et al. | |
| 4,505,890 A | 3/1985 | Jain et al. | |
| 4,543,370 A | 9/1985 | Porter et al. | |
| 4,572,833 A | 2/1986 | Pedersen et al. | |
| 4,576,646 A | 3/1986 | Branco et al. | |
| 4,601,894 A | 7/1986 | Hanna et al. | |
| 4,643,894 A | 2/1987 | Porter et al. | |
| 4,652,313 A | 3/1987 | Den Boer et al. | |
| 4,661,162 A | 4/1987 | Kurihara et al. | |
| 4,683,256 A | 7/1987 | Porter et al. | |
| 4,690,822 A | 9/1987 | Uemura et al. | |
| 4,695,467 A | 9/1987 | Uemura et al. | |
| 4,695,591 A | 9/1987 | Hanna et al. | |
| 4,725,441 A | 2/1988 | Porter et al. | |
| 4,775,536 A | 10/1988 | Patell | |
| 4,802,924 A | 2/1989 | Woznicki et al. | |
| 4,816,259 A | 3/1989 | Matthews et al. | |
| 4,820,524 A | 4/1989 | Berta | |
| 4,820,529 A | 4/1989 | Uchida et al. | |
| 4,828,841 A | 5/1989 | Porter et al. | |
| 4,853,230 A | 8/1989 | Lovgren et al. | |
| 4,853,249 A | 8/1989 | Takashima et al. | |
| 4,880,636 A | 11/1989 | Franz | |
| 4,886,669 A | 12/1989 | Ventouras | |
| 4,892,742 A | 1/1990 | Shah | |
| 4,897,270 A | 1/1990 | Deutsch et al. | |
| 4,904,476 A | 2/1990 | Mehta et al. | |
| 4,913,893 A | 4/1990 | Varco et al. | |
| 4,917,885 A | 4/1990 | Chiba et al. | |
| 4,948,622 A | 8/1990 | Kokubo et al. | |
| 4,965,089 A | 10/1990 | Sauter et al. | |
| 4,981,698 A * | 1/1991 | Cherukuri et al. ................. 426/5 |
| 4,999,189 A | 3/1991 | Kogan et al. | |
| 5,009,897 A | 4/1991 | Brinker et al. | |
| 5,023,108 A | 6/1991 | Bagaria et al. | |
| 5,026,560 A | 6/1991 | Makino et al. | |
| 5,059,416 A | 10/1991 | Cherukuri et al. | |
| 5,064,650 A | 11/1991 | Lew | |
| 5,077,053 A * | 12/1991 | Kuncewitch et al. ......... 424/441 |
| 5,082,669 A | 1/1992 | Shirai et al. | |
| 5,098,715 A | 3/1992 | McCabe et al. | |
| 5,136,031 A | 8/1992 | Khan et al. | |
| 5,146,730 A | 9/1992 | Sadek et al. | |
| 5,164,195 A | 11/1992 | Lew | |
| 5,186,930 A | 2/1993 | Kogan et al. | |
| 5,198,227 A | 3/1993 | Batista et al. | |
| 5,209,933 A | 5/1993 | MacFarlane et al. | |
| 5,213,738 A | 5/1993 | Hampton et al. | |
| 5,228,909 A | 7/1993 | Burdick et al. | |
| 5,228,916 A | 7/1993 | Berta | |
| 5,248,516 A | 9/1993 | Wheatley et al. | |
| 5,252,339 A | 10/1993 | Cristofori et al. | |
| 5,286,502 A | 2/1994 | Meyers | |
| 5,296,233 A | 3/1994 | Batista et al. | |
| 5,382,435 A | 1/1995 | Geary et al. | |
| 5,393,333 A | 2/1995 | Trouve | |
| 5,409,711 A | 4/1995 | Mapelli et al. | |
| 5,411,746 A | 5/1995 | Signorino et al. | |
| 5,415,871 A | 5/1995 | Pankhania et al. | |
| 5,422,121 A | 6/1995 | Lehmann et al. | |
| 5,425,950 A | 6/1995 | Dandiker et al. | |
| 5,433,960 A * | 7/1995 | Meyers ............................ 426/5 |
| 5,436,026 A | 7/1995 | Berta | |

(Continued)

FOREIGN PATENT DOCUMENTS

EP    0056825 B1    8/1982

(Continued)

OTHER PUBLICATIONS

U.S. Appl. No. 10/122,498, filed Apr. 15, 2002. U.S. Appl. No. 60/325,726, filed Sep. 28, 2001.
U.S. Appl. No. 60/291,127, filed Nov. 15, 2001.
U.S. Appl. No. 10/122,531, filed Apr. 15, 2002.
U.S. Appl. No. 10/211,139, filed Apr. 15, 2002.
U.S. Appl. No. 10/122,999, filed Apr. 12, 2002.
USP 24, 2000 Version, 19-20 and 856 (1999).
Light, "Modified Food Starches: Why, What, Where and How", (adapted from Modified Food Starch's Symposium at AACCs 74th Annual Meeigng Oct. 29-Nov. 2, 1989).
Pharmacia Remington, Preformulacion, p. 2241-2242, summary attached.
Remington: "The Science & Practice of Pharmacy". pp. 208-209 (2000).
Remington: "The Science & Practice of Pharmacy", pp. 1625-1630 (17th Ed.) (1985).
Fegely, K., "The Effect of Tablet Shape on the Perception of High Gloss Film Coating Systems", www.colorcon.com (2002).
Tricor Systems WGbss 3.4 Model 805A/806H Surface Analysis System Reference Manual (1996).

(Continued)

*Primary Examiner* — Zohreh A Fay

(57) ABSTRACT

Water soluble, gelatin-free dip coatings for substrates comprising a hydrocolloid, such as carrageenan, and sucralose.

18 Claims, 1 Drawing Sheet

U.S. PATENT DOCUMENTS

| | | |
|---|---|---|
| 5,445,829 A | 8/1995 | Paradissis et al. |
| 5,447,726 A | 9/1995 | Nomura |
| 5,459,983 A | 10/1995 | Sadek et al. |
| 5,464,633 A | 11/1995 | Conte et al. |
| 5,470,581 A | 11/1995 | Grillo et al. |
| 5,474,786 A | 12/1995 | Kotwal et al. |
| 5,480,479 A | 1/1996 | Signorino |
| 5,482,718 A | 1/1996 | Shah et al. |
| 5,496,561 A | 3/1996 | Okada et al. |
| 5,498,709 A | 3/1996 | Navia |
| 5,506,248 A | 4/1996 | Nikfar et al. |
| 5,512,314 A | 4/1996 | Signorino et al. |
| 5,514,384 A | 5/1996 | Signorino |
| 5,525,354 A | 6/1996 | Posti et al. |
| 5,534,263 A | 7/1996 | Wong et al. |
| 5,538,125 A | 7/1996 | Berta |
| 5,560,926 A | 10/1996 | Franz et al. |
| 5,571,533 A | 11/1996 | Santus et al. |
| 5,591,455 A | 1/1997 | Signorino |
| 5,593,694 A | 1/1997 | Hayashida et al. |
| 5,595,592 A | 1/1997 | Signorino et al. |
| 5,614,218 A | 3/1997 | Olsson et al. |
| 5,622,721 A | 4/1997 | Dansereau et al. |
| 5,630,871 A | 5/1997 | Jordan |
| 5,633,015 A | 5/1997 | Gilis et al. |
| 5,635,208 A | 6/1997 | Parekh et al. |
| 5,641,513 A | 6/1997 | Lech et al. |
| 5,641,536 A | 6/1997 | Lech et al. |
| 5,650,169 A | 7/1997 | Conte et al. |
| 5,658,589 A | 8/1997 | Parekh et al. |
| 5,667,573 A | 9/1997 | Kondou |
| 5,667,802 A | 9/1997 | Grimberg |
| 5,679,406 A | 10/1997 | Berta |
| 5,681,584 A | 10/1997 | Savastano et al. |
| 5,681,585 A | 10/1997 | Oshlack et al. |
| 5,681,684 A | 10/1997 | Kinashi et al. |
| 5,685,589 A | 11/1997 | Kikuchi et al. |
| 5,690,960 A | 11/1997 | Bengtsson et al. |
| 5,698,220 A | 12/1997 | Cardinal et al. |
| 5,707,648 A | 1/1998 | Yiv |
| 5,712,310 A | 1/1998 | Koch |
| 5,725,880 A | 3/1998 | Hirakawa et al. |
| 5,733,575 A | 3/1998 | Mehra et al. |
| 5,738,874 A | 4/1998 | Conte et al. |
| 5,750,148 A | 5/1998 | Maruyama et al. |
| 5,756,123 A | 5/1998 | Yamamoto et al. |
| 5,770,225 A | 6/1998 | Parekh et al. |
| 5,776,479 A | 7/1998 | Pallos et al. |
| 5,792,473 A | 8/1998 | Gergely et al. |
| 5,800,836 A | 9/1998 | Morella et al. |
| 5,807,580 A | 9/1998 | Luber |
| 5,814,336 A | 9/1998 | Kelm et al. |
| 5,814,339 A | 9/1998 | Prudhoe |
| 5,830,503 A | 11/1998 | Chen |
| 5,843,479 A | 12/1998 | Kelm et al. |
| 5,863,559 A | 1/1999 | Phillips et al. |
| 5,885,617 A | 3/1999 | Jordan |
| 5,891,474 A | 4/1999 | Busetti et al. |
| 5,908,638 A | 6/1999 | Huber et al. |
| 5,914,132 A | 6/1999 | Kelm et al. |
| 5,919,485 A | 7/1999 | Cochran et al. |
| 5,922,352 A | 7/1999 | Chen et al. |
| 5,935,602 A | 8/1999 | Dansereau et al. |
| 5,945,124 A | 8/1999 | Sachs et al. |
| 5,968,551 A | 10/1999 | Oshlack et al. |
| 6,022,564 A | 2/2000 | Takechi et al. |
| 6,039,976 A | 3/2000 | Mehra et al. |
| 6,051,255 A | 4/2000 | Conley et al. |
| 6,066,336 A | 5/2000 | Ullah et al. |
| 6,068,856 A | 5/2000 | Sachs et al. |
| 6,077,533 A | 6/2000 | Oshlack et al. |
| 6,077,541 A | 6/2000 | Chen et al. |
| 6,080,426 A | 6/2000 | Amey et al. |
| 6,083,430 A | 7/2000 | Fuisz et al. |
| 6,096,340 A | 8/2000 | Chen et al. |
| 6,113,945 A | 9/2000 | Jacobs et al. |
| 6,120,801 A | 9/2000 | Parekh et al. |
| 6,120,802 A | 9/2000 | Breitenbach et al. |
| 6,123,964 A | 9/2000 | Asgharnejad et al. |
| 6,129,933 A | 10/2000 | Oshlack et al. |
| 6,156,343 A | 12/2000 | Morita et al. |
| 6,165,513 A | 12/2000 | Dansereau et al. |
| 6,183,808 B1 | 2/2001 | Grillo et al. |
| 6,190,692 B1 | 2/2001 | Busetti et al. |
| 6,210,714 B1 | 4/2001 | Oshlack et al. |
| 6,214,376 B1 | 4/2001 | Gennadios |
| 6,214,378 B1 | 4/2001 | Tanida et al. |
| 6,214,380 B1 | 4/2001 | Parekh et al. |
| 6,228,400 B1 | 5/2001 | Lee et al. |
| 6,238,704 B1 | 5/2001 | Suzuki et al. |
| 6,245,350 B1 | 6/2001 | Amey et al. |
| 6,245,356 B1 | 6/2001 | Baichwal |
| 6,248,363 B1 | 6/2001 | Patel et al. |
| 6,270,804 B1 | 8/2001 | Getz |
| 6,274,162 B1 | 8/2001 | Steffenino et al. |
| 6,274,173 B1 | 8/2001 | Sachs et al. |
| 6,294,200 B1 | 9/2001 | Conte et al. |
| 6,309,666 B1 | 10/2001 | Hatano et al. |
| 6,309,668 B1 | 10/2001 | Bastin et al. |
| 6,340,473 B1 | 1/2002 | Tanner et al. |
| 6,348,090 B1 | 2/2002 | Grillo et al. |
| 6,420,473 B1 | 7/2002 | Chittamuru et al. |
| 6,488,962 B1 | 12/2002 | Berner et al. |
| 6,521,257 B1 | 2/2003 | Taniguchi et al. |
| 6,579,545 B2 | 6/2003 | Zyck et al. |
| 6,635,282 B1 | 10/2003 | Flanagan et al. |
| 7,429,619 B2 | 9/2008 | Kamath |
| 2001/0000471 A1 | 4/2001 | Shen et al. |
| 2001/0036476 A1 | 11/2001 | Oshlack et al. |
| 2001/0046511 A1 | 11/2001 | Zerbe et al. |

FOREIGN PATENT DOCUMENTS

| | | |
|---|---|---|
| EP | 246693 B1 | 11/1987 |
| EP | 0470872 B1 | 2/1992 |
| EP | 0575179 A | 12/1993 |
| EP | 0638310 A | 2/1995 |
| EP | 0 684 301 A2 | 11/1995 |
| EP | 0 717 992 A2 | 6/1996 |
| EP | 714656 | 6/1996 |
| EP | 0714656 A | 6/1996 |
| EP | 0839527 A | 5/1998 |
| EP | 974344 A2 | 1/2000 |
| EP | 1112738 | 4/2001 |
| EP | 1117736 | 7/2001 |
| EP | 0 934 734 B1 | 10/2002 |
| FR | 2 783 832 A | 3/2000 |
| GB | 1543167 | 3/1979 |
| JP | 63062535 A | 3/1988 |
| JP | 1067645 | 3/1989 |
| JP | 2-48521 | 2/1990 |
| JP | 3279325 | 12/1991 |
| JP | 8-99875 | 4/1996 |
| JP | 7-501073 | 4/1997 |
| JP | 10066556 A | 3/1998 |
| JP | 11180864 | 7/1999 |
| WO | WO 9007859 A | 7/1990 |
| WO | WO 9115548 A | 10/1991 |
| WO | WO 95/03063 A | 2/1995 |
| WO | WO 95/23594 A1 | 9/1995 |
| WO | WO 98/27151 | 6/1998 |
| WO | WO 98/30341 A | 7/1998 |
| WO | WO 99/46329 A1 | 9/1999 |
| WO | WO 99/51210 A1 | 10/1999 |
| WO | WO 00/18835 A | 3/2000 |
| WO | WO 00/18835 A1 | 4/2000 |
| WO | WO 00/32174 A2 | 6/2000 |
| WO | WO 00/42998 A1 | 7/2000 |
| WO | WO 00/45794 A1 | 8/2000 |
| WO | WO 00/48574 A1 | 8/2000 |
| WO | WO 01/03677 A | 1/2001 |
| WO | WO 0103677 A | 1/2001 |
| WO | WO 01/07507 A1 | 2/2001 |
| WO | WO 01/26633 A1 | 4/2001 |
| WO | WO 01/26634 A | 4/2001 |
| WO | WO 01/91721 A2 | 12/2001 |

OTHER PUBLICATIONS

"Purity® Gum 59" Technical Services Bulletin, 1993.

Zallie, "The Role and Function of Specialty Starches in the Confection Industry" Brochure, pp. 1-16 (1997).

Zallie. "New Starches for Gelling and Non-gelling Applications" reprinted from Manufacturing Confectioner (Nov. 1988).

FMC Biopolymer Brochure, "Carragenan", available at www.fmcbiopolymer.com on Apr. 2, 2001.

Polyvinylpyrrolidone for the Pharmaceutical Industry, Brochure by BASF, pp. 15 and 107-108 (Aug. 1993).

Specifications and Test Methods for Eudragit®, pp. 1-3 (1996).

Applicability of the Monograh... EUDRAGIT® S30D, pp. 1 (1994).

Gulian, Frank et al., "Color and Gloss Uniformity of Tablets Coated in a Side-Vented Pan Using Opaglos® 2"; Poster Reprint, American Association of Pharmaceutical Scientists, pp. 1-5, Oct. 2001.

European Search Report, EP 02256752 dated May 28, 2003.

European Search Report for EP 02 25 3341 dated Mar. 21, 2003.

European Search Report for EP 02 25 3342 dated Mar. 19, 2003.

EP Search Report dated Apr. 20, 2007 for EP Application No. 06 07 7180.

Pharmacia Remington, Preformulacion, p. 2241-2242, English summary of underlined sections is attached, available prior to Jun. 21, 2002.

* cited by examiner

FILM FORMING COMPOSITIONS CONTAINING SUCRALOSE

CROSS-REFERENCE TO RELATED APPLICATION

This Application claims the benefit of U.S. Application No. 60/325,727 filed on Sep. 28, 2001, which is incorporated by reference in its entirety herein.

FIELD OF THE INVENTION

This invention relates to novel, water soluble, gelatin-free compositions for dip coating substrates, such as tablets and capsules, and methods for producing such tablets and capsules.

BACKGROUND OF THE INVENTION

During most of this century, hard gelatin capsules were a popular dosage form for prescription and over-the-counter (OTC) drugs. The ability to combine capsule halves having different colors provided manufacturers with a unique means of distinguishing various pharmaceutical products. Many patients preferred capsules over tablets, perceiving them as being easier to swallow. This consumer preference prompted pharmaceutical manufacturers to market certain products in capsule form even when they were also available in tablet form.

Generally, empty hard gelatin capsules are manufactured using automated equipment. This equipment employs rows of stainless steel pins, mounted on bars or plates, which are dipped into a gelatin solution maintained at a uniform temperature and fluidity. The pins are then withdrawn from the gelatin solution, rotated, and then inserted into drying kilns through which a strong blast of filtered air with controlled humidity is forced. A crude capsule half is thus formed over each pin during drying. Each capsule half is then stripped, trimmed to uniform length, filled and joined to an appropriate mating half.

An alternative to capsule products are caplets, which generally are solid, oblong tablets that are often coated with various polymers such as cellulose ethers to improve their aesthetics, stability, and swallowability. Typically, such polymers are applied to the tablets either from solution in organic solvents, or from aqueous dispersion via spraying. However, such spray-coated tablets lack the shiny surface and elegance of the hard gelatin capsules. Additionally, it is not commercially feasible to spray-coat a tablet with a different color coating on each end.

Another alternative to capsule products are "gelcaps," which are elegant, shiny, consumer-preferred, dosage forms that are prepared by dipping each half of an elongated tablet in two different colors of gelatin solution. See U.S. Pat. Nos. 4,820,524; 5,538,125; 5,685,589; 5,770,225; 5,198,227; and 5,296,233, which are all incorporated by reference herein. A similar dosage form, commercially available as a "geltab," is prepared by dipping each half of a generally round, convex tablet into different colors of gelatin solution, as described in U.S. Pat. No. 5,228,916, U.S. Pat. No. 5,436,026 and U.S. Pat. No. 5,679,406, which are all incorporated by reference herein. As used herein, such "gelcaps" and "geltabs" shall be included within the broader term, "tablets."

However, the use of gelatin as a pharmaceutical coating material presents certain disadvantages and limitations, including the potential for decreased dissolution rate after extended storage due to cross-linking of the gelatin and potential for microbial contamination of the gelatin solution during processing. Further, the energy-related costs associated with gelatin coatings tend to be high since the gelatin material is typically applied to the substrates at an elevated temperature of at least about 40° C. in order to maintain fluidity of the gelatin, while the substrates are maintained at about 50° C. in order to minimize microbial growth.

Various attempts have been made to produce gelatin-free hard shell capsules. For example, WO 00/18835 discloses the combination of starch ethers or oxidized starch and hydrocolloids for use in preparing hard capsule shells via conventional dip molding processing. See also U.S. Pat. No. 4,001,211 (capsules prepared via pin dip coating with thermogelled methylcellulose ether compositions). However, due to potential tampering concerns, hard gelatin capsules are no longer a preferred delivery system for consumer (over-the-counter) pharmaceuticals, dietary supplements, or other such products. Additionally, the properties of an ideal composition into which steel pins are to be dipped then dried to form hard capsule shells thereon are not necessarily the same as those for dipping tablets to form a coating thereon. For example, relevant physical properties such as viscosity, weight-gain, film thickness, tensile strength, elasticity, and moisture content will differ between compositions for hard capsule formation and for coating tablets. See e.g., U.S. Pat. No. 1,787,777 (Optimal temperatures of the substrate and coating solution, residence times in the solution, and drying conditions differ.)

One disadvantage associated with dipping tablets or capsules into a non-gelatin coating system is that resulting coatings often lack adequate physical properties, e.g., tensile strength, plasticity, hardness, and thickness. Although the inclusion of plasticizers thereto may improve the plasticity properties of the coatings, such non-gelatin coating systems often disadvantageously result in tablets having soft, tacky coatings without a hardness sufficient to maintain their shape or smoothness during handling. In addition, many non-gelatin compositions do not adhere to the tablet substrate in an amount sufficient to uniformly cover the tablet after a single dipping. Further, many non-gelatin compositions lack the sufficient rheological properties necessary to maintain uniform color dispersion throughout the dipping and drying process. Attempts have been made to improve the rheological properties of these compositions by, for example, increasing their solids content in order to increase viscosity. However, such compositions often disadvantageously resulted in undesirable coating aesthetics such as surface roughness, decreased gloss, and non-uniform coating thickness.

Film forming compositions comprising hydrocolloids have been described in WO 00/18835 and WO 99/46329. However, these compositions incorporate 0.01 to 5 percent by weight of the hydrocolloids as a "setting system" in combination with known film-forming polymers such as polyvinyl alcohol, starch ethers, or oxidized starch.

One hydrocolloid, carrageenan, has been used in film coatings for pharmaceutical applications. However, carrageenan by itself was considered to be too weak for coating pharmaceutical tablets, and thus was required to be combined with microcrystalline cellulose for satisfactory coating results. See WO 00/45794. Not only is the addition of the cellulose to the carrageenan not economically advantageous, but the viscosity of the resulting mixture is also difficult to control. Moreover, the inclusion of the cellulose in such coatings tends to hinder the overall dissolution rate of the coating, which thereby delays the release time of the active contained therein.

It is desirable to find a dip coating material, which not only produces a similar elegant, shiny, high gloss, consumer-preferred dosage form similar to that of gelatin-coated forms, but which is absent the limitations of gelatin, particularly those noted above.

It is further desirable to find such a coating material suitable for use in dip coating operations, which does not inhibit the dissolution of the active coated therewith.

SUMMARY OF THE INVENTION

The present invention provides for a film forming composition comprising, consisting of, and/or consisting essentially of:

a) carrageenan; and
b) sucralose.

We have found that when a dosage form is coated with the composition of the present invention, the result is an elegant, shiny, high gloss, consumer-preferred dosage form similar to that of a gelatin-coated form, but which lacks the limitations associated with gelatin, particularly those noted above. We have also found that when such a composition is used in dip coating operations, it does not inhibit the dissolution of the active coated therewith.

DETAILED DESCRIPTION OF THE INVENTION

Figure 1A:
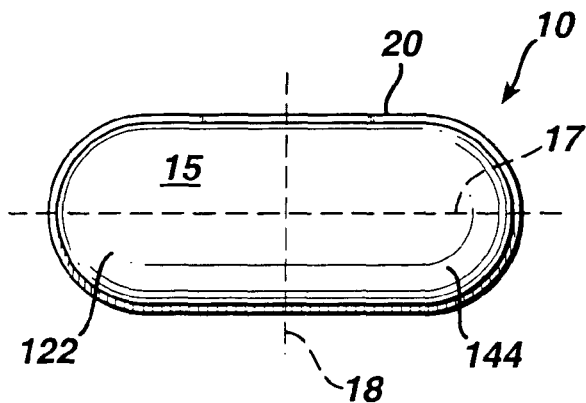
FIG. 1A is an enlarged, schematic top plan view of an oblong convex core of a first configuration, the bottom plan view being identical thereto.

As used herein, "capsules" refer to hard or soft shell compartments that enclose a dosable ingredient. "Tablets," as used herein, refer to compressed or molded solid dosage forms of any shape or size. "Caplets," as used herein, refer to solid, oblong-shaped tablets. "Gelcaps" refer to solid caplets having a glossy gelatinous coating, and "geltabs" refer to solid tablets having a flat belly-band, or side, convex opposing faces, and a glossy gelatinous coating. "Hardness" as used herein in connection with films or coatings indicates the resistance of the film/coating to deformation upon impact. "Water soluble" or "water solubilize," as used herein in connection with non-polymeric materials, shall mean from sparingly soluble to very soluble, i.e., not more than 100 parts water required to dissolve 1 part of the non-polymeric, water soluble solute. See Remington, "The Science and Practice of Pharmacy," pages 208-209 (2000). "Water soluble" or "water solubilize," as used herein in connection with polymeric materials, shall mean that the polymer swells in water and can be dispersed at the molecular level to form a homogeneous dispersion or colloidal "solution." "Surface gloss", as used herein, shall mean a measure of reflected light, as determined by the method set forth in detail in example 8 herein.

Dimethicone is a well known pharmaceutical material consisting of linear siloxane polymers containing repeating units of the formula $\{-(CH_2)_2SiO\}_n$ stabilized with trimethylsiloxy end blocking units of the formula $\{(CH_3)_3SiO-\}$. Simethicone is the mixture of dimethicone and silicon dioxide. For the purposes of this invention, the two materials may be used interchangably.

The first embodiment of this invention is directed to water soluble, substantially gelatin-free, film forming compositions. One composition comprises, consists of, and/or consists essentially of a hydrocolloid, such as carrageenan, and sucralose. As used herein, "substantially gelatin-free" shall mean less than about 0.1 percent, e.g. less than about 0.01 percent, of animal derived gelatin in the composition.

Any hydrocolloid known in the art is suitable for use in the film forming composition of the present invention. Examples of such hydrocolloids include, but are not limited to, alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan, and derivatives and mixtures thereof. In one embodiment, the hydrocolloid comprises, consists essentially of, and/or consists of at least about 50%, i.e. at least about 75%, or at least about 90% of carrageenan.

Carrageenans are polysaccharides that are comprised of repeating galactose units and 3,6-anhydrogalactose units. Examples of carrageenans suitable for use in the present invention include, but are not limited to the naturally derived carrageenans, such as the grades further defined below as iota, kappa, and lambda carrageenan and derivatives thereof. A rich source of iota carrageenan is the seaweed *Eucheuma spinosum*. The approximate content of anhydrogalactose units in iota carrageenan is, based upon the total weight of iota carrageenan, about 30% whereas kappa carrageenan has, based upon the total weight of kappa carrageenan, about 34% anhydrogalactose units and lambda carrageenan is essentially devoid of these units.

Carrageenans may also be characterized by the amount of ester sulfate groups that are present on both its galactose and anhydrogalactose units. The ester sulfate content of iota carrageenan may range from, based upon a total weight of iota carrageenan, from about 25% to about 34%, e.g. about 32%. This is intermediate between kappa carrageenan, which has about a 25 weight % ester sulfate content, and lambda carrageenan, which has about a 35 weight % ester sulfate content. The sodium salt of iota carrageenan is generally soluble in cold water, but different grades of iota carrageenan may require heating water to different temperatures to solubilize them.

Metal cations may be employed in the compositions of the present invention for the purpose of optimizing the gelling properties of the carrageenan. Suitable cations include mono-, di-, and tri-valent cations. Suitable sources of cations include organic and inorganic salts, which may be used in an amount, based upon the total dry weight of the composition of the present invention, from 0 to about 5 percent, e.g. from about 1 percent to about 4.5 percent. In one embodiment the metal cation may be selected from K+, Na+, Li+, Ca++, Mg++, and mixtures thereof.

Sucralose, which is also known as 4,1,6'-trideoxy-galactosucrose, is a high intensity sweetener that may be produced in accordance with the process disclosed in U.K. Patent No. 1,544,167, and U.S. Pat. Nos. 5,136,031 and 5,498,709, which are incorporated by reference herein.

In one embodiment, the film forming composition contains, based upon the total dry solids weight of the composition, from about 0.5 percent to about 20 percent, e.g. from about 1 percent to about 15 percent, from about 3 to about 9 percent, or from about greater than 5 to about 9 percent hydrocolloid such as carrageenan, and from about 75 percent to about 99.5 percent, e.g. from about 80 percent to about 99 percent, or from about 83 percent to about 95 percent sucralose.

These film forming compositions are typically in the form of a dispersion for ease of dip coating substrates therein or spraying substrates therewith. Such dispersions contain solvent in an amount, based upon the total weight of the dispersion, from about 70 percent to about 99 percent, for example, from about 78 percent to about 95 percent, or from about 80 percent to about 90 percent. Examples of suitable solvents include, but are not limited to water; alcohols such as methanol, ethanol, and isopropanol; organic solvents such as methylene chloride, acetone, and the like; and mixtures thereof. In one embodiment, the solvent is water. The resulting film forming dispersion typically possesses a solids level of, based upon the total weight of the film forming dispersion, from about 1 percent to about 30 percent, e.g. from about 5 percent to about 22 percent, or from about 10 percent to about 20 percent.

In one embodiment, the film forming composition for dip coating contains, based upon the total wet weight of the dipping composition, from about 0.05 percent to about 5 percent, e.g. from about 0.1 percent to about 2 percent or from about 0.5 percent to about 1.5 percent, of hydrocolloid such as carrageenan, and from about 1 percent to about 30 percent, e.g. from about 5 percent to about 20 percent or from about 10 percent to about 15 percent, sucralose.

In one particular embodiment, the hydrocolloid comprises, consists of, or consists essentially of a carrageenan.

Optionally, the film forming composition may further comprise other ingredients such as, based upon the total weight of the dipping solution, from about 0 percent to about 40 percent plasticizers, from about 0 percent to about 2 percent preservatives such as methyl paraben and ethyl paraben, from about 0 percent to about 14 percent opacifying agents such as titanium dioxide, and/or from about 0 percent to about 14 percent colorants. See *Remington's Practice of Pharmacy*, Martin & Cook, 17$^{th}$ ed., pp. 1625-30, which is herein incorporated by reference.

Any plasticizer known in the pharmaceutical art is suitable for use in the present invention, and may include, but not be limited to polyethylene glycol; glycerin; sorbitol; triethyl citrate; triethyl amine; tribuyl citrate; dibutyl sebecate; vegetable oils such as castor oil; surfactants such as polysorbates, sodium lauryl sulfates, and dioctyl-sodium sulfosuccinates; propylene glycol; mono acetate of glycerol; diacetate of glycerol; triacetate of glycerol; natural gums and mixtures thereof.

Any coloring agent suitable for use in pharmaceutical application may be used in the present invention and may include, but not be limited to azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant gree BS, red 2G, azorubine, ponceau 4R, amaranth, D&C red 33, D+C red 22, D+C red 26, D+C red 28, D+C yellow 10, FD+C yellow 5, FD+C yellow 6, FD+C red 3, FD+C red 40, FD+C blue 1, FD+C blue 2, FD+C green 3, brilliant black BN, carbon black, iron oxide black, iron oxide red, iron oxide yellow, titanium dioxide, riboflavin, carotenes, antyhocyanines, turmeric, cochineal extract, clorophyllin, canthaxanthin, caramel, betanin, and mixtures thereof.

In one embodiment, the pharmaceutical dosage form is comprised of: a) a core; b) an optional first coating layer on the surface of the core comprised of a subcoating that substantially covers the core; and c) a second coating layer substantially covering the surface of the first coating layer, with the second coating layer comprised of the film forming composition of the present invention. As used herein, "substantially covers" shall mean at least about 95 percent of the surface area of the underlying substrate is covered by the given coating. For example, with respect to the first coating layer and the second coating layer, at least about 95% of the surface of the first coating layer is covered by the second coating layer.

In another embodiment, the pharmaceutical dosage form is comprised of: a) a core; b) an optional first coating layer on the surface of the core comprised of a subcoating that covers a portion of the core; and c) a second coating layer that covers a portion of the surface of the first coating layer, with the second coating layer comprised of the film forming composition of the present invention. As used herein, "portion" shall mean a part of the dosage form having a surface area that is equal to or less than about 95 percent of the surface area of the underlying substrate.

Figure 2:
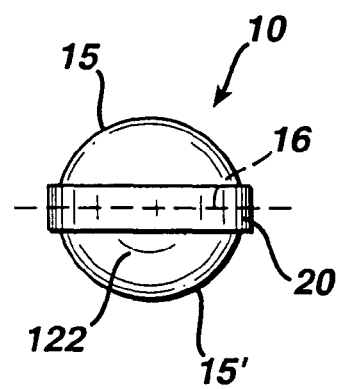
FIG. 2 is an enlarged, schematic elevational end view of the oblong convex core of FIGS. 1A and 1B, the opposite elevational end view being identical thereto.
Figure 3:
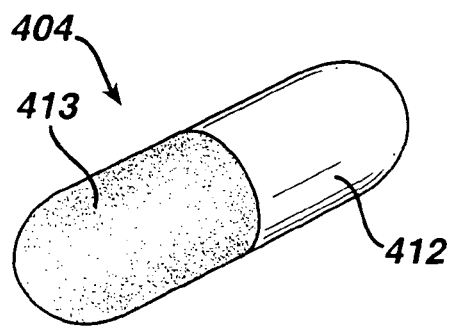
FIG. 3 is a perspective view of an exemplary tablet 404 of the present invention having a first coating portion 412 of one visual distinction and a second coating portion 413 having a second visual distinction.

In yet a further embodiment, the second coating layer may be comprised of a plurality of coating portions. An example of this embodiment comprised of two coating portions is illustrated in FIG. 2, in which the dosage form 404 is coated with a first coating portion 412 and a second coating portion 413. Although the dosage form in FIG. 2 indicates that at least one of such portions is visually and/or chemically distinct from at least one other portion, it is conceived that one or more of the portions may be visually and/or chemically similar in nature. For example, each end of a tablet may be coated with dip coatings of different colors to provide a distinctive appearance for specialty products. See U.S. Pat. No. 4,820,524, which is incorporated by reference herein.

Figure 1B:
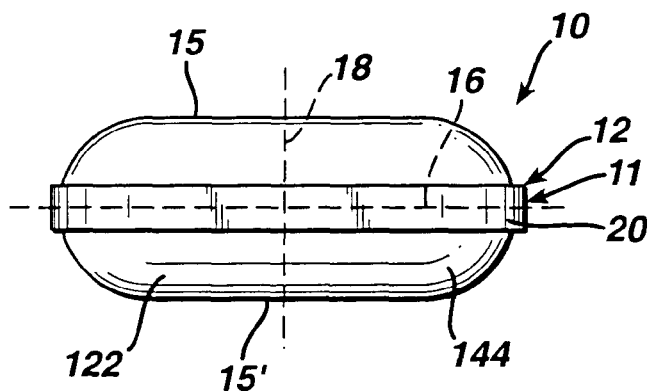
FIG. 1B is an enlarged, schematic elevational side view of the oblong convex core of FIG. 1A, having a face 15, a "belly band" or side 11, and an edge or corner 12, the opposite elevational side view being identical thereto.

The core, or substrate, of the present invention may be a solid dosage form of any size or shape. Suitable cores include compressed or molded tablets, hard or soft capsules, confectionery based forms such as for example lozenges, nougats, or fondants, and the like. Cores are available in various shapes and configurations. For example, FIGS. 1A, 1B and 2 illustrate an oblong convex core 10 having an oblong shape and two rounded ends 122, 144, as viewed from the top, bottom or sides (see FIGS. 1A and 1B). The oblong convex core 10 may also have two oppositely positioned convex surfaces 15, 15' and a raised portion therebetween, referred to as a land 20 (shown most clearly in FIGS. 1B and 2).

It is noted that the length of the oblong core 10 is an imaginary line (not shown per se, but which is commensurate with a portion of the dotted line 16 that is within the core 10 shown in FIG. 1B) which extends the distance between the ends 122, 144 of the oblong core 10. The height of the oblong core 10 is another imaginary line (not shown per se, but which is commensurate with a portion of the dotted line 18 that is within the core 10 shown in FIG. 1B) which extends the distance between the two opposite convex surfaces 15, 15' of the core 10, midway of the length. The width of the oblong core is a third imaginary line (not shown per se, but which is commensurate with a portion of the dotted line 16 that is within the core 10 shown in FIG. 2) which extends the distance between opposite sides of the core 10, perpendicular to and midway of the core's length and height (and which may intersect the land 20 of the core 10, if present).

Any number of active agents may be contained in the dosage form. The active agents may be contained in the core, in the optional first coating layer, and/or in the second coating layer. In one embodiment an active agent is contained in the core.

In an alternate embodiment, a first active agent may be contained in the first coating layer, and the core may contain a second active agent and/or an additional amount of the first active agent. In yet another embodiment, the active agent may be contained in the first coating layer, and the core may be substantially free, i.e., contain less than about 1 percent, e.g. less than about 0.1 percent, of active agent.

The use of subcoatings is well known in the art and disclosed in, for example, U.S. Pat. No. 3,185,626, which is incorporated by reference herein. Any composition suitable for film-coating a tablet may be used as a subcoating according to the present invention. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Additional suitable subcoatings include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating may be comprised of, based upon the total weight of the subcoated tablet, from about 2 percent to about 8 percent, e.g. from about 4 percent to about 6 percent of a water-soluble cellulose ether and from about 0.1 percent to about 1 percent castor oil, as disclosed in detail in U.S. Pat. No. 5,658,589, which is incorporated by reference herein. In another embodiment, the subcoating may be comprised of, based upon the total weight of the subcoating, from about 20 percent to about 50 percent, e.g., from about 25 percent to about 40 percent of HPMC; from about 45 percent to about 75 percent, e.g., from about 50 percent to about 70 percent of maltodextrin; and from about 1 percent to about 10 percent, e.g., from about 5 percent to about 10 percent of PEG 400.

The dried subcoating typically is present in an amount, based upon the dry weight of the core, from about 0 percent to about 10 percent, e.g. from about 0 percent to about 5 percent. The dried dip coating layer typically is present in an amount, based upon the dry weight of the core and the optional subcoating, from about 1.5 percent to about 10 percent.

The average thickness of the dried dip coating layer typically is from about 30 microns to about 400 microns. However, one skilled in the art would readily appreciate without undue experimentation that the dip coating thickness may be varied in order to provide a smoother, easier to swallow, dosage form or to achieve a desired dissolution profile.

The thickness of gelatin dipped film coatings often varies at different locations on the substrate depending upon the shape of the substrate. For example, the thickness of a gelatin dipped coating at an edge or corner (see, e.g., edge 12 in FIG. 1) of a substrate may be as much as 50 percent to 70 percent less than the thickness of that coating near the center of a major face of the substrate (see, e.g. face 15 in FIG. 1). However, coatings comprised of the composition of the present invention have relatively less variance in thickness when applied via dip coating to a substrate.

In one embodiment, the exterior layer or "shell" of the present invention advantageously possesses a high surface gloss. The surface gloss of the shell and/or the exterior surface of the dosage form is preferably at least about 150 gloss units, e.g. at least about 175 gloss units, or at least about 190 gloss units when measured by the method set forth in Example 8 herein.

The film forming compositions of the present invention may be prepared by combining, based upon the total amount of sucralose, from about 80% to about 99% of the sucralose and the cationic metal-containing compound such as potassium or calcium salts, in water with mixing at a temperature of about 75° C. to about 80° C., wherein the water is used in an amount sufficient to dissolve the sucralose. While maintaining constant temperature and mixing, the remainder of the sucralose (approximately equal to the amount of the hydrocolloid) and the hydrocolloid are added thereto. In an alternative embodiment, the remainder of the sucralose and the hydrocolloid may first be combined with mixing under ambient conditions until the resulting mixture is homogeneous, then this preblend may be added to the cation solution, either before or after the addition of the remaining portion of the sucralose. Any optional ingredients may then be added to the resulting mixture at constant mixing.

Surprisingly, substrates may be dipped into such film forming compositions of the present invention using the same equipment and range of process conditions as used for the production of dip molded, gelatin-coated capsules and tablets, with the exception of dipping solution temperature. Typically, the dip-coating solution of the present invention is both heated and mixed during the dipping process. Suitable temperature of the dipping solution is from about 20° C. to about 100° C., e.g. from about 40° C. to about 80° C., or from about 55° C. to about 65° C. Dipping solution temperature may be varied within these ranges by increasing or decreasing the cationic strength of the solution, e.g. higher temperatures are required at higher cationic strength, while lower dipping temperatures are suitable at lower cationic strengths. Details of such equipment and processing conditions are well-known in the art and are disclosed at, for example, U.S. Pat. No. 4,820,524 (caplets) and WO 00/18835 (capsules), which are incorporated by reference herein.

The tablets coated with the film forming composition of the present invention may contain one or more active agents. The term "active agent" is used herein in a broad sense and may encompass any material that can be carried by or entrained in the system. For example, the active agent can be a pharmaceutical, nutraceutical, vitamin, dietary supplement, nutrient, herb, foodstuff, dyestuff, nutritional, mineral, supplement, or favoring agent or the like and combinations thereof.

The active agents useful herein can be selected from classes from those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; antiulcer agents; anti-uricemic agents; anxiolytic agents; appetite stimulants; appetite suppressants; beta-blocking agents; bronchodilators; cardiovascular agents; cerebral dilators; chelating agents; cholecystekinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatory drugs (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents that may be used in the invention include, but are not limited to: acetaminophen; acetic acid; acetylsalicylic acid, including its buffered forms; acrivastine; albuterol and its sulfate; alcohol; alkaline phosphatase; allantoin; aloe; aluminum acetate, carbonate, chlorohydrate and hydroxide; alprozolam; amino acids; aminobenzoic acid; amoxicillin; ampicillin; amsacrine; amsalog; anethole; ascorbic acid; aspartame; astemizole; atenolol; azatidine and its maleate; bacitracin; balsam peru; BCNU (carmustine); beclomethasone diproprionate; benzocaine; benzoic acid; benzophenones; benzoyl peroxide; benzquinamide and its hydrochloride; bethanechol; biotin; bisacodyl; bismuth subsalicylate; bornyl acetate; bromopheniramine and its maleate; buspirone; caffeine; calamine; calcium carbonate, casinate and hydroxide; camphor; captopril; cascara sagrada; castor oil; cefador; cefadroxil; cephalexin; centrizine and its hydrochloride; cetirizine; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleates and tannates; chlorpromazine; cholestyramine resin; choline bitartrate; chondrogenic stimulating protein; cimetidine; cinnamedrine hydrochloride; citalopram; citric acid; clarithromycin; clemastine and its fumarate; clonidine; clorfibrate; cocoa butter; cod liver oil; codeine and its fumarate and phosphate; cortisone acetate; ciprofloxacin HCl; cyanocobalamin; cyclizine hydrochloride; cyproheptadine; danthron; dexbromopheniramine maleate; dextromethorphan and its hydrohalides; diazepam; dibucaine; dichloralphenazone; diclofen and its alkali metal sales; diclofenac sodium; digoxin; dihydroergotamine and its hydrogenates/mesylates; diltiazem; dimethicone; dioxybenzone; diphenhydramine and its citrate; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fexofenadine; fluoxetine; folic acid; fosphenytoin; 5-fluorouracil (5-FU); fluoxetine; flurbiprofen; furosemide; gabapentan; gentamicin; gemfibrozil; glipizide; glycerine; glyceryl stearate; granisetron; griseofulvin; growth hormone; guafenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and dinitrates; isoxicam; ketamine; kaolin; ketoprofen; lactic acid; lanolin; lecithin; leuprolide acetate; lidocaine and its hydrochloride salt; lifinopril; liotrix; loperamide, loratadine; lovastatin; luteinizing hormore; LHRH (lutenizing hormone replacement hormone); magnesium carbonate, hydroxide, salicylate, and trisilicate; meclizine; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methsergide and its maleate; methyl nicotinate; methyl salicylate; methyl cellulose; methsuximide; metoclopramide and its halides/hydrates; metronidazole; metoprotol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerine; nonoxynol-9; norethindrone and its acetate; nystatin; octoxynol; octoxynol-9; octyl dimethyl PABA; octyl methoxycinnamate; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentastatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine; phenytoin; pirmenol; piroxicam and its salts; polymicin B sulfate; potassium chloride and nitrate; prazepam; procainamide hydrochloride; procaterol; promethazine and its hydrochloride; propoxyphene and its hydrochloride and napsylate; pramiracetin; pramoxine and its hydrochloride salt; prochlorperazine and its maleate; propanolol and its hydrochloride; promethazine and its hydrochloride; propanolol; pseudoephedrine and its sulfates and hydrochlorides; pyridoxine; pyrolamine and its hydrochlorides and tannates; quinapril; quinidine gluconate and sulfate; quinestrol; ralitoline; ranitadine; resorcinol; riboflavin; salicylic acid; scopolamine; sesame oil; shark liver oil; simethicone; sodium bicarbonate, citrate, and fluoride; sodium monofluorophosphate; sucralfate; sulfanethoxazole; sulfasalazine; sulfur; sumatriptan and its succinate; tacrine and its hydrochloride; theophylline; terfenadine; thiethylperazine and its maleate; timolol and its maleate; thioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; tripolidine hydrochloride; undecylenic acid; vancomycin; verapamil HCl; vidaribine phosphate; vitamins A, B, C, D, $B_1$, $B_2$, $B_6$, $B_{12}$, E, and K; witch hazel; xylometazoline hydrochloride; zinc; zinc sulfate; zinc undecylenate. Active agents may further include, but are not limited to food acids; insoluble metal and mineral hydroxides, carbonates, oxides, polycarbophils, and salts thereof; adsorbates of active drugs on a magnesium trisilicate base and on a magnesium aluminum silicate base, and mixtures thereof. Mixtures and pharmaceutically acceptable salts of these and other actives can be used.

We have unexpectedly found that the coatings formed by dipping substrates into the compositions of the present invention possess excellent properties comparable to those possessed by gelatin coatings, e.g. crack resistance, hardness, thickness, color uniformity, smoothness, and gloss. Additionally, tablets dip coated with the compositions of the present invention are superior to tablets dip coated with conventional gelatin-based coatings in several important ways. First, tablets dip coated with the compositions of the present invention advantageously retain acceptable dissolution characteristics for the desired shelf-life and storage period at elevated temperature and humidity conditions. Advantageously, the compositions of this invention possess a relatively shorter setting time relative to that of gelatin-containing compositions. Beneficially, the resulting dried coatings therefrom contained fewer air bubbles relative to the amount present in dried, gelatin based dipping compositions, and possessed a relatively more uniform coating thickness, i.e., the thickness at the tablet edges 12 is comparable to that at the face 15 as shown in the tablet 10 illustrated in FIG. 1. In addition, the dip coated compositions of the present invention possessed a gloss measurement of greater than 150 gloss units, for example greater than 190 gloss units, which is a higher degree of glossiness relative to similar coatings applied via spray coating method known in the art. See U.S. Pat. No. 6,274,162.

A further advantage of the film-forming compositions of the present invention is that the resulting coated pharmaceutical has a sweet taste without the inclusion of sugar. Not only will this improve a patient's compliance with taking the prescribed pharmaceutical, but also it will not promote tooth decay or increase caloric intake like sugar coated products. Moreover, the sugar-free coating is especially suitable for diabetic users and those restricting sugars from their diets. In addition, sugar coatings disadvantageously are relatively less stable than sucralose coatings, and thus often react with other components in the coating and discolor. Yet further, the sucralose coatings of the present invention do not provide a nutritional source for potential microbial contamination as do sugar coated products.

We have further unexpectedly found that the combination of a polysaccharide hydrocolloid, such as carrageenan, and sucralose, which is not a film forming component, forms an effective film coating on substrates in the substantial absence of a film former or strengthening polymer, e.g., celluloses, starches, pullulan, polyvinylpyrrolidone, derivatives thereof, and mixtures thereof. Examples of such cellulosics include, but are not limited to, hydroxypropylmethylcellulose, microcrystalline cellulose, hydroxyethylcellulose, hydroxypropylcellulose, ethylcellulose, cellulose acetate, and mixtures thereof. By "substantial absence" it is meant less than, based upon the total weight of the film forming composition, 1%, e.g., less than 0.5% or less than 0.1% or from about 0.01% to about 1%. The substantial absence of such film formers and strengthening polymers in the coating beneficially improves the ability of the coating to immediately release the active coated therewith. In embodiments wherein controlled, prolonged, delayed, extended, or sustained release is of importance, such film formers or polymers may be added to the coating in an amount, based upon the total dry weight of the coating composition, from about 5% to about 95% percent, e.g. from about 20% to about 75%.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

1. Film-Forming Property Analysis of Sucralose

A 10% solution of sucralose in water was prepared, then poured into in a 3-inch glass Petri dish such that the solution was about 2 mm deep therein. The solution was then dried in an oven at 70° C. for about 6 hours. The resulting dried material adhered to the glass dish, but could not be peeled off as a film. The material also crumbled when scraped. These results indicated that sucralose alone will not form a film of acceptable physical properties, e.g., tensile strength, plasticity, hardness.

2. Preparation of a Sucralose-Carrageenan Solution

A dipping solution having the components set forth below was prepared as follows:

| Dipping solution ingredients: | |
|---|---|
| Purified Water | 100 g |
| Potassium Chloride crystals | 0.400 g |
| Kappa-carrageenan* | 1.000 g |
| Sucralose** | 10.00 g |
| FD&C Red No. 40 | 0.090 g |
| Titanium dioxide | 0.500 g |

*Kappa carrageenan was grade "GP-911NF", obtained from FMC Corporation
**Sucralose was obtained from McNeil Specialty Products Company Sucralose and Kappa-carrageenan were pre-blended using a mortar and pestle.

In a separate container, potassium chloride was added to the water with stirring at a temperature of 75° C. until the potassium chloride was dissolved therein. After increasing the temperature of the resulting solution to 90° C., the sucralose-kappa-carrageenan pre-blend was gradually added thereto with mixing using an electric mixer (Janke and Kunkel, IKA Labortechnik, Staufen, Germany) with propeller blade at a rate of approximately 700 rpm until homogeneous. After the mixing was discontinued, the solution was then cooled. At a temperature of about 50° C., the solution began to gel. After reheating the solution to a temperature of 80° C., the Red No. 40 and titanium dioxide were added thereto with mixing at 600 rpm until homogeneous. The solution was then recirculated through a shallow dish and heated to maintain a temperature of 60° C.

A portion of the above solution was poured into a 3-inch aluminum tray such that the depth of the solution in the dish was about 2 mm. The sample was then dried in an oven at 70° C. for about 6 hours. The resulting dried solution material adhered to the glass dish, and was peeled off as one cohesive circular film approxmately 2-inches in diameter (after some shrinkage). The film possessed acceptable tensile strength, hardness and plasticity, as well as surprisingly high transparency.

3. Preparation of a Sucralose-Carrageenan Solution

A dipping solution having the components set forth below was prepared as follows:

| Dipping solution ingredients: | |
|---|---|
| Purified Water | 90 g |
| Potassium Chloride crystals | 0.350 g |
| Kappa-carrageenan* | 0.500 g |
| Sucralose** | 15.00 g |
| Yellow color dispersion*** | 0.090 g |

*Kappa carrageenan was grade "GP-911NF", obtained from FMC Corporation
**Sucralose was obtained from McNeil Specialty Products Company
***Yellow color dispersion was "Opatint" ® No. DD2125" obtained from Colorcon, Inc., Sucralose and Kappa-carrageenan were pre-blended using a mortar and pestle.

In a separate container, potassium chloride was added to the water with stirring at a temperature of 80° C. until the potassium chloride was dissolved therein. While maintaining a constant temperature, the sucralose-Kappa-carrageenan pre-blend was gradually added thereto with mixing using the mixer of Example 2 at a rate of about 800 rpm. The yellow color dispersion was then added thereto with constant mixing until homogeneous. The resulting solution was then recirculated through a shallow vessel while maintaining constant temperature.

4. Dip Coating Substrates with a Sucralose-Carrageenan Dispersion

Subcoated acetaminophen caplets, which were prepared according to the method disclosed in U.S. Pat. No. 6,214,380 (Example 1, steps A through H), which is incorporated by reference herein, were hand-dipped into the solution prepared in Example 2 at a temperature of 60° C., then the coated caplets were dried for 10 minutes under ambient conditions.

The resulting dried dipped tablets possessed a hard, non-tacky coating with a high gloss, a smooth surface, and an even color distribution. No bubbles were visually observed. The tablet edges were also well-covered.

5. Dip Coating Substrates with a Sucralose-Carrageenan Dispersion

The procedure set forth in Example 4 was repeated with additional subcoated acetaminophen caplets, but using the solution prepared in Example 3.

The resulting dried dipped tablets possessed a hard, non-tacky coating with a lower gloss relative to that of the caplets coated with the solution of Example 2. The dried dipped tablets possessed a smooth surface and an even color distribution. No bubbles were visually observed. The tablet edges were also well-covered.

6. Preparation of Sucralose-Kappa Carrageenan Dispersion, and Tablets coated therewith.

A dipping solution having the components set forth below was prepared as follows:

| | |
|---|---|
| Purified Water | 890.5 g |
| Potassium Chloride crystals | 4 g |
| Kappa-carrageenan* | 5 g |
| Sucralose** | 100 g |
| Yellow No. 10 Dye (FD&C) | 0.5 g |

*Kappa carrageenan was grade "GP-911NF", obtained from FMC Corporation
**Sucralose was obtained from McNeil Specialty Products Company Sucralose and carrageenan were pre-blended using a mortar and pestle.

In a separate container, potassium chloride was added to the water at a temperature of 80° C., and slowly mixed until the potassium chloride was dissolved therein. The sucralose and carrageenan blend was then added to the potassium chloride solution with vigorous mixing (approximately 700 rpm) using the electric mixer of Example 2. The resulting mixture formed a uniform dispersion without clumps. While the mixture was cooling, the Yellow No. 10 Dye was added with continued mixing. The resulting solution was then recirculated through a shallow vessel (using a peristaltic pump at 60 g/minute) while maintaining constant temperature of about 62° C.

The dipping procedure set forth in Example 4 was then repeated with additional subcoated acetaminophen caplets, but using the solution prepared in the present Example.

The resulting dried dipped tablets possessed a hard, non-tacky coating, a smooth surface and an even color distribution. The tablet edges were also well-covered.

7. Preparation of Sucralose-Iota/Kappa Carrageenan (mixture) Dispersion, and Tablets coated therewith.

A dipping solution having the components set forth below was prepared as follows:

| | |
|---|---|
| Purified Water | 890.5 g |
| Potassium Chloride crystals | 2 g |
| Calcium Chloride crystals | 1.5 g |
| Kappa-carrageenan* | 5 g |
| Iota-carrageenan*** | 5 g |
| Sucralose** | 100 g |
| Yellow No. 10 Dye (FD&C) | 0.25 g |

*Kappa carrageenan was grade "GP-911NF", obtained from FMC Corporation
**Sucralose was obtained from McNeil Specialty Products Company
***Iota carrageenan was Marine Colloids Grade "GP-379NF," obtained from FMC Corporation A dip-coating solution was prepared from the above ingredients according to the manner described in Example 6. The dipping procedure set forth in Example 4 was then repeated with additional subcoated acetaminophen caplets, but using the solution prepared in the present Example. This dipping process resulted in a weight gain of approximately 80 mg per tablet (40 mg per half tablet).

Example 8

Surface Gloss Measurement of Coated Tablets

One (1) tablet made according to Example 4 and one (1) other tablet made according to Example 5 were tested for surface gloss using an instrument available from TriCor Systems Inc. (Elgin, Ill.) under the tradename, "Tri-Cor Model 805A/806H Surface Analysis System" and generally in accordance with the procedure described in "TriCor Systems WGLOSS 3.4 Model 805A/806H Surface Analysis System Reference Manual" (1996), which is incorporated by reference herein, except as modified below, This instrument utilized a CCD camera detector, employed a flat diffuse light source, compared tablet samples to a reference standard, and determined average gloss values at a 60 degree incident angle. During its operation, the instrument generated a gray-scale image, wherein the occurrence of brighter pixels indicated the presence of more gloss at that given location.

The instrument also incorporated software that utilized a grouping method to quantify gloss, i.e., pixels with similar brightness were grouped together for averaging purposes.

The "percent full scale" or "percent ideal" setting (also referred to as the "percent sample group" setting), was specified by the user to designate the portion of the brightest pixels above the threshold that will be considered as one group and averaged within that group. "Threshold", as used herein, is defined as the maximum gloss value that will not be included in the average gloss value calculation. Thus, the background, or the non-glossy areas of a sample were excluded from the average gloss value calculations. The method disclosed in K. Fegley and C. Vesey, "The Effect of Tablet Shape on the Perception of High Gloss Film Coating Systems", which is available at www.colorcon.com as of Mar. 18, 2002 and incorporated by reference herein, was used in order to minimize the effects resulting from different tablet shapes, and to report a metric that was comparable across the industry.(Selected the 50% sample group setting as the setting which best approximated analogous data from tablet surface roughness measurements.).

After initially calibrating the instrument using a calibration reference plate (190-228; 294 degree standard; no mask, rotation 0, depth 0), a standard surface gloss measurement was then created using gel-coated caplets available from McNEIL-PPC, Inc. under the tradename, "Extra Strength Tylenol Gelcaps." The average gloss value for a sample of 112 of such gel-coated caplets was then determined, while employing the 25 mm full view mask (190-280), and configuring the instrument to the following settings:
Rotation: 0
Depth: 0.25 inches
Gloss Threshold: 95
% Full Scale: 50%
Index of Refraction: 1.57
   The average surface gloss value for the reference standard was determined to be 269.

Each sample of coated tablets was then independently tested in accordance with the same procedure.

A 2-tablet sample prepared according to the method of Example 4 possessed an average surface gloss of 211 gloss units.

Additional samples of other, commercially available gel coated tablets were also tested in accordance with the same procedure and compared to the same standard. The results are summarized in Table L below.

TABLE L

Gloss values of commercially available coated tablets

| Product | Motrin IB* Caplet (white) | Excedrin** Aspirin free Caplets (red) | Excedrin** Migraine Geltab (green side) | Excedrin** Migraine Geltab (white side) | Extra Strength Tylenol Geltabs* (yellow side) | Extra Strength Tylenol Geltabs* (red side) |
|---|---|---|---|---|---|---|
| Type of coating | sprayed film | sprayed film | gelatin enrobed | gelatin enrobed | dipped | dipped |
| No. of tablets tested | 41 | 40 | 10 | 10 | 112 | 112 |
| Gloss Value (gloss units) | 125 | 119 | 270 | 264 | 268 | 268 |

*Available from McNEIL-PPC, Inc.
**Available from Bristol-Myers, Squibb, Inc.

This Example showed that the tablets coated with the compositions of the present invention possessed a high surface gloss value (e.g. 211 gloss units in this example) that was comparable to that possessed by commercially-available gelatin coated tablets. In contrast, typical sprayed films possessed a substantially lower surface gloss, e.g. 119 to 125 gloss units in this Example.

I claim:

1. A pharmaceutical dosage form comprising a core having an outer coating, said outer coating comprising, based upon the dry weight of the coating:
   a) carrageenan; and
   b) sucralose, wherein the coating is comprised of, based upon the total dry weight of the coating,
   a) from about 0.5 percent to about 20 percent of carrageenan; and
   b) from about 75 percent to about 99.5 percent of sucralose.

2. The pharmaceutical dosage form of claim 1, wherein the coating is comprised of, based upon the total dry weight of the coating:
   a) from about 5 percent to about 9 percent of carrageenan; and
   b) from about 83 percent to about 95 percent of sucralose.

3. The pharmaceutical dosage form of claim 1, wherein the carrageenan is kappa carrageenan.

4. The pharmaceutical dosage form of claim 1 wherein the coating further comprises, based upon the total dry weight of the coating, from about 0 to about 40 percent plasticizers.

5. The pharmaceutical dosage form of claim 4 wherein the plasticizers are selected from the group consisting of polyethylene glycol, glycerol, sorbitol, sucrose, corn syrup, fructose, dioctyl-sodium sulfosuccinate, triethyl citrate, tribuyl citrate, 1,2-propylene glycol, mono acetate of glycerol, diacetate of glycerol, triacetate of glycerol, natural gums, and mixtures thereof.

6. The pharmaceutical dosage form of claim 1 wherein the coating further comprises, based upon the total dry weight of the coating, from about 0 percent to about 14 percent of a coloring agent.

7. The pharmaceutical dosage form of claim 6 wherein the coloring agent is selected from the group consisting of azo dyes, quinopthalone dyes, triphenylmethane dyes, xanthene dyes, indigoid dyes, iron oxides, iron hydroxides, titanium dioxide, natural dyes, and mixtures thereof.

8. The pharmaceutical dosage form of claim 1 further comprising a plurality of outer coatings, wherein at least a first portion of the dosage form is comprised of a first outer coating and at least a second portion of the dosage form is comprised of a second outer coating.

9. The pharmaceutical dosage form of claim 8 wherein the second outer coating is visually distinct from the first outer coating.

10. A pharmaceutical dosage form comprising a core, a subcoating substantially covering said core, and an outer coating substantially covering said subcoating, wherein the outer coating is comprised of, based upon the dry weight of the outer coating,
   a) from about 0.5 percent to about 20 percent of carrageenan; and
   b) from about 75 percent to about 99.5 percent of sucralose.

11. The coated dosage form of claim 10 wherein the subcoating comprises cellulose ethers, plasticizers, polycarbohydrates, pigments, opacifiers, and mixtures thereof.

12. The dosage form of claim 1 having a surface gloss of at least about 150 gloss units.

13. The dosage form of claim 2 having a surface gloss of at least about 150 gloss units.

14. The pharmaceutical dosage form of claim 1 comprising an effective amount of a pharmaceutical active ingredient, wherein said dosage form meets USP dissolution requirements for immediate release forms of said pharmaceutical active ingredient.

15. A method of making coated tablets comprising dip coating tablets with an aqueous dispersion under conditions sufficient to form a coating on the tablets, said aqueous dispersion comprising:

a) solvent;
b) carrageenan; and
c) sucralose, wherein the coating is comprised of, based upon the total dry weight of the coating,
  i) from about 0.5 percent to about 20 percent of carrageenan; and
  ii) from about 75 percent to about 99.5 percent of sucralose.

16. The pharmaceutical dosage form of claim 1 wherein the coating further comprises, based upon the total weight of the coating, from about 0.001 percent to about 1 percent of a film former.

17. The pharmaceutical dosage form of claim 16 wherein the film former is selected from the group consisting of cellulose, starch, polyvinylpyrrolidone, derivatives and mixtures thereof.

18. The pharmaceutical dosage form of claim 1, wherein the coating is comprised of less than about 5% of cations, based upon the total weight of the coating.

* * * * *